United States Patent
Mahadevan

(10) Patent No.: US 11,288,718 B2
(45) Date of Patent: Mar. 29, 2022

(54) SYSTEM AND METHOD TO SIMPLIFY MEDICAL BILLING FOR HOSPITALISTS

(71) Applicant: Uma Mahadevan, Cupertino, CA (US)

(72) Inventor: Uma Mahadevan, Cupertino, CA (US)

(*) Notice: Subject to any disclaimer, the term of this patent is extended or adjusted under 35 U.S.C. 154(b) by 329 days.

(21) Appl. No.: 16/567,168

(22) Filed: Sep. 11, 2019

(65) Prior Publication Data

US 2021/0073877 A1    Mar. 11, 2021

(51) Int. Cl.
| | |
|---|---|
| *G06Q 30/04* | (2012.01) |
| *G06Q 10/10* | (2012.01) |
| *G16H 40/20* | (2018.01) |
| *G16H 10/60* | (2018.01) |
| G16H 15/00 | (2018.01) |
| G06Q 40/08 | (2012.01) |

(52) U.S. Cl.
CPC ........... *G06Q 30/04* (2013.01); *G06Q 10/107* (2013.01); *G16H 10/60* (2018.01); *G16H 40/20* (2018.01); *G06Q 40/08* (2013.01); *G16H 15/00* (2018.01)

(58) Field of Classification Search
CPC ........ G16H 10/60; G16H 40/20; G16H 40/67; G16H 40/63; G16H 70/60; G16H 15/00; G16H 20/10; G16H 40/40; G16H 50/20; G16H 70/20; G06Q 10/10; G06Q 10/06; G06Q 30/04; G06Q 40/08; G06Q 10/107
See application file for complete search history.

(56) References Cited

U.S. PATENT DOCUMENTS

| | | | |
|---|---|---|---|
| 9,643,722 B1* | 5/2017 | Myslinski | G06K 9/00711 |
| 2009/0204434 A1* | 8/2009 | Breazeale, Jr. | G06Q 30/04 |
| | | | 705/3 |
| 2011/0227740 A1* | 9/2011 | Wohltjen | G01S 11/16 |
| | | | 340/573.1 |
| 2017/0262614 A1* | 9/2017 | Vishnubhatla | G16H 50/20 |
| 2019/0214116 A1* | 7/2019 | Eberting | G16H 50/30 |
| 2019/0320898 A1* | 10/2019 | Dirghangi | A61B 3/15 |
| 2020/0005783 A1* | 1/2020 | Judy | G16H 40/67 |
| 2020/0020454 A1* | 1/2020 | McGarvey | G06Q 30/0282 |

* cited by examiner

*Primary Examiner* — Maroun P Kanaan
(74) *Attorney, Agent, or Firm* — Young Basile Hanlon & MacFarlane, P.C.

(57) ABSTRACT

A method for automated medical billing includes retrieving details of one or more encounters between a patient and a medical provider from a hospital software. A user input is obtained via a user interface on a medical provider computing device, wherein the user interface enables the medical provider to initiate automated billing of the patient after each encounter. Thereafter, a geo-location of the medical provider, a micro-location of the patient in hospital, a time associated with an encounter, and an identity of the patient and the medical provider are automatically sensed, and a bed number of the patient, a current time, a geo-location, an identification number of the medical provider, and a charge associated with the encounter is sent to the billing server. Finally, a claim form is automatically filled by the billing server, based on the received information; and the filled claim form is transmitted to a payment entity.

13 Claims, 10 Drawing Sheets

| Service | Patient class | Level 1 | Level 2 | Level 3 | Level 4 | Level 5 |
|---|---|---|---|---|---|---|
| Admit | Observation | 99218 | 99219 | 99220 | | |
| Admit | Inpatient | 99221 | 99222 | 99223 | | |
| Follow up | Observation | 99224 | 99225 | 99226 | | |
| Follow up | Inpatient | 99231 | 99232 | 99233 | | |
| Discharge, diff day | Observation | 99217 | | | | |
| Discharge, diff day | Inpatient | 99238 | 99239 | | | |
| Discharge, same day | N/A | 99234 | 99235 | 99236 | | |
| N/A | Consult, i/p | 99251 | 99252 | 99253 | 99254 | 99255 |
| N/A | Critical care | 99291 | 99291 + 99292 (additional code) | | | |

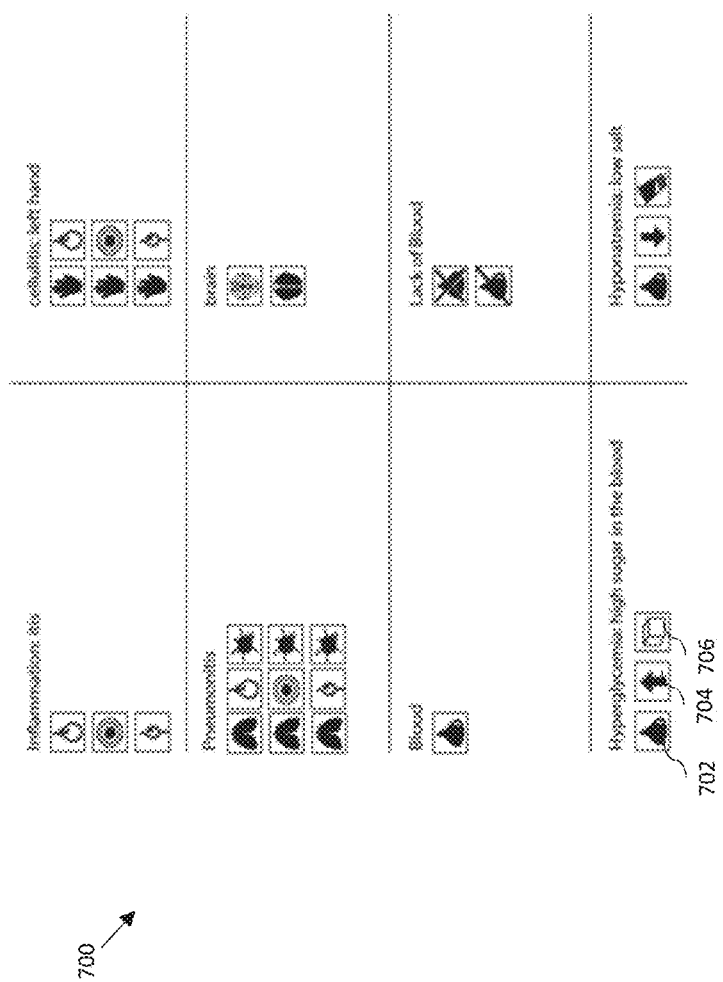

SYSTEM AND METHOD TO SIMPLIFY MEDICAL BILLING FOR HOSPITALISTS

TECHNICAL FIELD

The present disclosure relates generally to medical billing workflows for communicating between multiple enterprises in healthcare, such as hospitals, medical groups, billing companies, clearinghouses, insurances, and more particularly to automated assembling, packaging, validating and transporting of medical claim information from a medical provider to a payer.

BACKGROUND

An encounter is a meeting/medical consultation between a medical provider and a patient inside a facility such as a hospital. Examples of the medical provider include, but are not limited to, a hospital and a doctor. The details of each encounter can be assembled into a spreadsheet and shared with a payer for claiming the fees associated with the encounter. However, there is unnecessary data entry, by various parties in a typical medical billing workflow, before a medical claim is assembled. There are too many steps and entities, like Electronic Medical Records (EMRs), billers and clearinghouses, before assembled medical claims can reach payers. The adjudication piece, where billers call or email insurances to settle disputes about payment for the medical claims, is inefficient and time consuming.

A typical medical claim form such as CMS 1500 is a 33 field medical form that a medical provider submits, whenever an encounter happens between the medical provider and the patient. In the CMS 1500, some fields describe the patient, others describe the medical provider and remaining fields describe corresponding disease and procedure. Generally, doctors do not like to type anything repetitively, like the same patient name every day. They see a lot of patients every day and carry a lot of information about each patient in their head. They do not like any additional work caused due to things like billing. Patient names can be long and complicated sometimes, which may cause typing or speech recognition errors. In order to avoid typing of long names, most billing applications show the full list of patients to the doctors and let them browse and choose a name of the patient. However, it is difficult to search or look up a patient in a list, as these lists can be long. Further, existing billing systems are cumbersome, need too many clicks and effort from the medical providers.

Hence, in view of the above, there exists a need for a system and method that facilitates automated assembling, packaging, validating and transporting of medical claim information from a medical provider to a payer, that overcomes the disadvantages associated with existing medical billing systems, and that reduces the effort and increase the efficiency of the medical provider.

SUMMARY

In an aspect of the present disclosure, there is provided a method for automated medical billing. The method includes retrieving details of one or more encounters between a patient and a medical provider from a hospital software. The method may further include obtaining a user input via a user interface on a medical provider computing device, wherein the user interface enables the medical provider to initiate automated billing of the patient after each encounter. The method may further include automatically sensing a geo-location of the medical provider, a micro-location of the patient in hospital, a time associated with an encounter, and an identity of the patient and the medical provider, wherein the micro-location includes a bed number of the patient in the hospital. The method may further include transmitting a bed number of the patient, a current time, a geo-location, an identification number of the medical provider, and a charge associated with the encounter to the billing server. The method may further include automatically filling a claim form by the billing server, based on the received information, and transmitting the filled claim form to a payment entity.

In another aspect of the present disclosure, there is provided a system for automated medical billing. The system includes a billing server configured to retrieve details of one or more encounters between a patient and a medical provider from a hospital software, obtain a user input via a user interface on a user computing device of the medical provider, wherein the user interface enables the medical provider to initiate automated billing of the patient after each encounter. The system further includes an assistant module configured to automatically sense a geo-location of the medical provider, a micro-location of the patient in hospital, a time associated with an encounter, and an identity of the patient and the medical provider, wherein the micro-location includes a bed number of the patient in the hospital, and transmit a bed number of the patient, a current time, a geo-location, an identification number of the medical provider, and a charge associated with the encounter to the billing server. The billing server is configured to automatically fill a claim form by the billing server, based on the received information, and send the filled claim form to a payment entity.

In another aspect of the present disclosure, there is provided a computer programmable product for automated medical billing, the computer programmable product comprising a set of instructions. The set of instructions when executed by a processor causes the processor to retrieve details of one or more encounters between a patient and a medical provider from a hospital software, provide a user interface on a user computing device of the medical provider, wherein the user interface enables the medical provider to initiate automated billing of the patient after each encounter, automatically sense a geo-location of the medical provider, a micro-location of the patient in hospital, a time associated with an encounter, and an identity of the patient and the medical provider, wherein the micro-location includes a bed number of the patient in the hospital, transmit a bed number of the patient, a current time, a geo-location, an identification number of the medical provider, and a charge associated with the encounter to the billing server, automatically fill a claim form by the billing server, based on the received information, and send the filled claim form to a payment entity.

Various embodiments of the present disclosure provide an ultra-customized, smart, slick, elegant system for physician and hospitalist billing, and a disruptive and innovative approach to third party billing system for a hospitalist. The system can be configured for other types of doctors in the future and maybe extended to facility billing. The system provides a billing bot that does 99% of the work for physician's billing, with very little left for the medical provider to do.

It will be appreciated that features of the present disclosure are susceptible to being combined in various combinations without departing from the scope of the present disclosure as defined by the appended claims.

DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to the following diagrams wherein:

FIG. 4 illustrate details stored in a database of the billing server, in accordance with an embodiment of the present disclosure;

FIG. 5A and FIG. 5B illustrate an exemplary claim form of type CMS 1500;

FIGS. 6A and 6B illustrates exemplary screenshots of the UI of the billing server, in accordance with an embodiment of the present disclosure;

FIG. 6C illustrates a spreadsheet formed based on the information represented by exemplary screenshot of FIG. 6B, in accordance with an embodiment of the present disclosure;

FIG. 7 illustrate a list of icons that can be added on an 'icon bar' on top of medical documents, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

Figure 1:
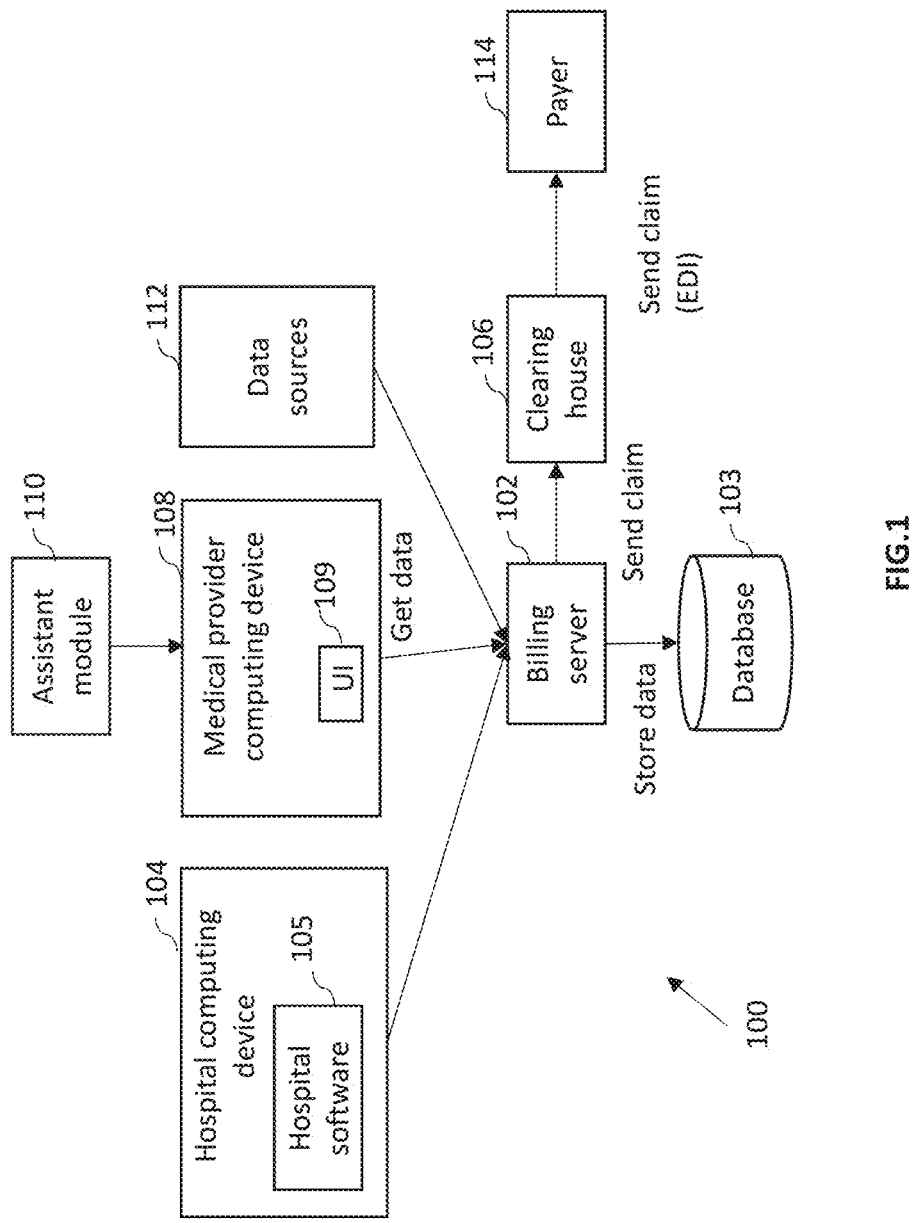
FIG. 1 illustrates an environment, wherein various embodiments of the present invention can be practiced.

FIG. 1 illustrates an environment 100, wherein various embodiments of the present invention can be practiced.

The environment 100 includes a billing server 102, an associated database 103 of the billing server 102 for storing data related to the billing server 102, a hospital computing device 104 executing a hospital software 105, a clearing house 106, a medical provider computing device 108 executing a User Interface (UI) 109 of the billing server 102, an assistant module 110 in communication with the medical provider computing device 108, data sources 112 in communication with the billing server 102, and a payer 114 in communication with the clearing house 106.

The medical provider computing device 108 may be carried by a medical provider such as a doctor/hospitalist during an encounter with a patient. An encounter is a meeting between the medical provider and a patient at a specific location at a certain time. The encounter happens at acute care hospitals, at the bedside of the patient. The encounter also happens when the patient gets admitted into the hospital. Most of the time, the patients come in through the Emergency room (ER), because they have some acute condition like Afib or COPD, that require hospitalization.

The payer 114 may be an insurance company such as Medicare, Aetna, Blue Cross Blue Shield, which is responsible for paying the medical group or individual medical providers for services rendered to a patient. The hospital software 105 is a large and expensive software that is typically used by hospital systems to store the medical information of each visit of a patient. An example of the hospital software 105 is an Electronic Medical Record (EMR). Typically, the medical provider has to fill in the details of each encounter with the patient in the hospital software 105.

The billing server 102 is a stand-alone billing platform that can be integrated with the hospital software 105 for automatically creating a medical claim for each encounter. In an embodiment of the present disclosure, the billing server 102 is configured to perform automated assembling, packaging, validating and transporting of medical claim information from the medical provider computing device 108 to the payer 114 based on the information received from the hospital software 105 and the UI 109. In an embodiment of the present disclosure, the UI 109 of the billing server 102 executes on a browser of the medical provider computing device 108 so as to receive information from the medical provider. Examples of the medical provider computing device 108 include, but are not limited to a mobile phone, a personal computer, a laptop, and a laptop.

Figure 2:
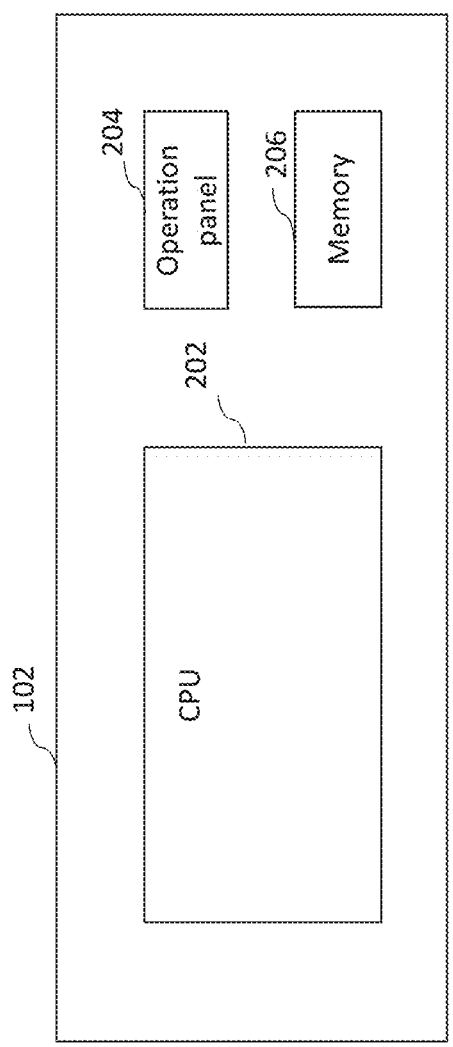
FIG. 2 illustrates a billing server of FIG. 1, in accordance with an embodiment of the present disclosure.

FIG. 2 illustrates the billing server 102, in accordance with an embodiment of the present disclosure. The billing server 102 includes a central processing unit (CPU) 202, an operation panel 204, and a memory 206. The CPU 202 is a processor, computer, microcontroller, or other circuitry that controls the operations of various components such as the operation panel 204, and the memory 206. The CPU 202 may execute software, firmware, and/or other instructions, for example, that are stored on a volatile or non-volatile memory, such as the memory 206, or otherwise provided to the CPU 202. The CPU 202 may be connected to the operation panel 204, and the memory 206, through wired or wireless connections, such as one or more system buses, cables, or other interfaces.

The memory 206, in addition to storing instructions and/or data for use by the CPU 202 in managing operation of the billing server 102, may also include user information associated with one or more users of the billing server 102. For example, the user information may include authentication information (e.g. username/password pairs), user preferences, and other user-specific information. The CPU 202 may access this data to assist in providing control functions (e.g. transmitting and/or receiving one or more control signals) related to operation of the operation panel 204, and the memory 206.

Referring back to FIG. 1, the clearinghouse 106 is an entity that sits between the billing server 102 and the payer 114. The primary role of the clearinghouse 106 is to accept information from the billing server 102 in a non-standard format, such as the Electronic Data Interchange (EDI) format. Examples of the clearinghouse 106 include, but are not limited to, Pokitdok™ and OfficeAlly™. In operation, the billing server 102 is configured to retrieve details of one or more encounters between a patient and a medical provider from the hospital software 105. In an example, the billing server 102 receives data from the hospital software 105 via Health Level (HL)7 files. The HL7 refers to a set of international standards for transfer of clinical and administrative data between software applications used by various healthcare providers. The HL7 files indicate the master list of encounters on any given day. For each encounter, it provides information about the patient, the medical provider 107, and the payer 114. In an example, information about each patient includes details such as insurance details, date of birth, gender and address. It is assumed herein, that the hospital software 105 has all the requisite information for their own billing process, and this information is being utilized by the billing server 102 for automatically preparing the claim form. The hospital software 105 may keep their files in a secure location, and the billing server 102 may read the files via secure FTP(sftp). The files may be generated once a day or more frequently, depending on the interface between the billing server 102 and the hospital software 105. Each file contains one or more events related to the encounters.

Figure 3:
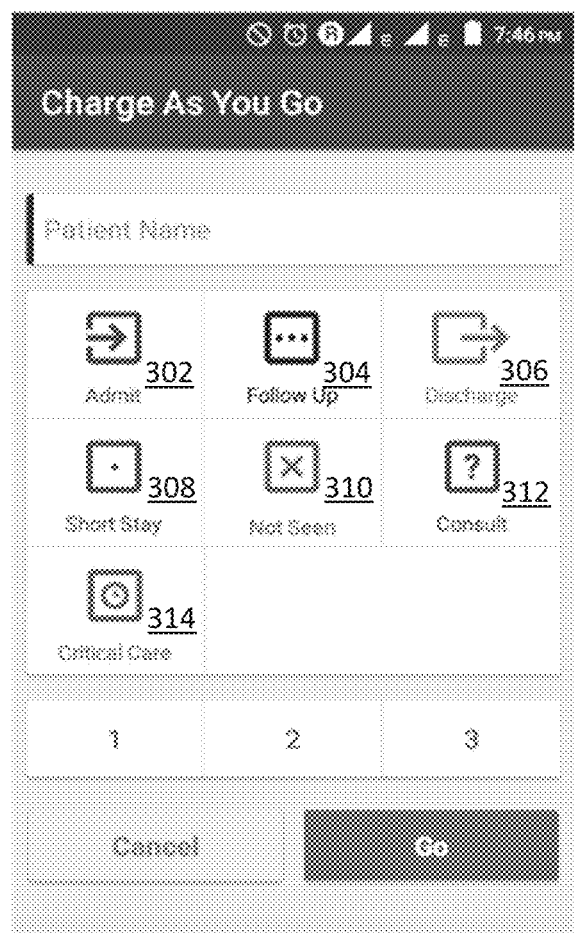
FIG. 3 illustrates an exemplary screenshot of a User Interface (UI) of a billing server of FIG. 1, in accordance with an embodiment of the present disclosure.

The billing server 102 is further configured to obtain a user input via a UI 109, wherein the UI 109 enables the medical provider to initiate automated billing of the patient after each encounter. FIG. 3 illustrates an exemplary screenshot 300 of the UI 109 for enabling the medical provider to charge a patient on the go, in accordance with an embodiment of the present disclosure. The screenshot 300 has only one screen and is operable by using at most 2 user clicks. The screenshot 300 illustrate various services such as admit 302, follow-up 304, discharge 306, short stay 308, not seen 310, consult 312, and clinical care 314 along with their icons. The screenshot 300 enables the medical provider to select a service, and also select a level '1', '2' or '3' of the selected service. In an embodiment of the present disclosure, some default levels may be predefined for the services. For example, service of type "admit" has default level '2'. The levels are an integral part of the billing for hospitalists and Current Procedural Terminology (CPT) codes are predefined according to the levels. In an example, if the type is 'admit' and level of service is '2', and if the patient status is 'Impatient', then corresponding CPT code is 99222, whereas it is 99223 if the level is '3'. The level signifies the care that was provided in the encounter.

In an example, the medical provider may type in patient name as 'Beto' and clicks on 'Discharge' and then 'level 1' and click on go. The status of the patient named 'Beto' may be changed from 'follow-up' to 'discharge, level 1' in corresponding details stored in the database 103. As soon as the medical provider clicks on 'Go', a confirmation message may be generated that "Your charge has been sent". Thus, the screenshot 300 enables the medical provider to enter their charges as soon as they leave the room of the patient. Alternatively, the medical provider may not need to type the patient name, and the patient name may be automatically detected based on automatic detection of patient's micro-location.

Referring back to FIG. 1, an automatic voice recognition and processing device (not shown) may be coupled to the medical provider computing device 108 for automatically recognizing the voice of the medical provider, and automatically providing one or more inputs to the UI 109. The automatic voice recognition and processing device may be associated with the patient's location, or it is placed next to the patient's bedside, or is moved along with the patient, if the patient changes rooms. In an example, the medical provider may provide a wake word for the voice assistant such as 'Ok zee, charge is discharge 2', or 'Ok zee, charge is discharge 2 for Smith', and the UI 109 records and receives the above-mentioned inputs.

Further, the assistant module 110 is configured to automatically sense a geo-location of the medical provider, a micro-location of the patient in hospital, a time associated with an encounter, and an identity of the patient and the medical provider, wherein the micro-location includes a bed number of the patient in the hospital; and transmit a bed number of the patient, a current time, a geo-location, an identification number of the medical provider, and a charge associated with the encounter to the billing server 102. Based on the information received, the billing server 102 is configured to automatically fill a claim form by the billing server 102, based on the received information, and send the filled claim form to the payer 114.

In an embodiment of the present disclosure, the assistant module 110 may include a location assistant, a geolocation assistant, a time assistant, an identity assistant, or any combination thereof.

The location assistant may include a beacon that detects a location of the patient, and provides this location to the UI 109. In an example, the beacon may be fixedly configured in a room and at bedside or placed in a pocket of the gown worn by the patient. In an example, the beacon device may be attached to a bed so that it emits the bed number (e.g., E 301-1, for a bed in floor 3 of a hospital in the East Wing). When the patient moves to a different location, the beacon may be reconfigured, and the mapping between the old room and the new room may be maintained in the billing server 102.

In an example, the beacon may include a Bluetooth device as a proxy for a patient in a fixed location such as a bed at a given time. As long as the patient is associated with this location, this proxy (for example the bed #+which hospital+ time) can be used wherever the patient needs to be referred. To make this work, a mechanism is needed that may map the proxy (the bed #, hospital, time) to a unique patient. The name of the patient corresponding to the bed location may be extracted from a database corresponding to the hospital software 105.

In another embodiment of the present disclosure, the location assistant may include a drone that flies inside a patient's room, detects a location of the patient, transmits the detected location to the billing server 102, and flies out from the patient's room. The billing server 102 may include a mapping list of bed number and patient details. Therefore, automatically determining a location of the patient also facilitates in automatically determining the patient's details and using them in preparing claim form.

In another embodiment of the present disclosure, the geo-location assistant provides information about latitude and longitude, from which the geo-location of the hospital can be determined. An example of the geo-location is {latitude: 26.1055035, longitude: −81.6848736}. This shows that this hospital is somewhere in Florida, which is 26 degrees North of the equator and 81 degrees west of the Greenwich Meridian. West=negative sign, and North=positive sign. Another hospital, whose geolocation is {−33.8567844, 151.2152967}, since it is South of the Equator and to the East of the meridian. The geo-location is referred to as macro location, while the bed number is referred to as micro location, as it specifies the location of the patient with greater specificity. The automated detection of macro and micro locations facilitates in automatically filling up the user details in the claim form that are associated with patient's location.

In yet another embodiment of the present disclosure, the time assistant provides information to the UI 109 regarding the current time and time zone of the patient, and the identity assistant provides information to the UI 109 regarding the patient. The automated detection of time of encounter and location of the same, facilitates in automatically filling up the user details in the claim form that are associated with patient's identity and time of encounter.

Based on the information received from the medical provider, and the assistant module 110, the UI 109 may send details to the billing server 102. Examples of the details include, but are not limited to, a bed number of the patient, a current time, a geo-location (latitude, longitude), doctor's identification (ID), and the fees charged by the doctor in the encounter.

The billing server 102 may further receive data from the data sources 112 such as National Plan and Provider Enumeration System (NPPES), where it may supply the National Provider Identifier (NPI) of a medical provider and obtain additional information, such as the name, address, phone, email etc. The NPI is a 10-digit identifier that is assigned by an organization NPPES. All the medical providers, hospitals, clearinghouses and health plans need this identifier. The billing server 102 keeps on adding and updating details about various encounters in their database 103 based on the information received from the UI 109.

FIG. 4 illustrate details 400 stored in a database of the billing server 102, in accordance with an embodiment of the present disclosure.

The details 400 show mapping from the icons in the UI 109 to actual procedure codes: 99219, 99220 etc. The patient status (Inpatient or Observation) is obtained based on data from the hospital software 105, the charge type (Admit/Follow up etc) and the charge level is obtained from the UI 109, and the two may be combined to get the CPT code that is needed.

Figure 5A:
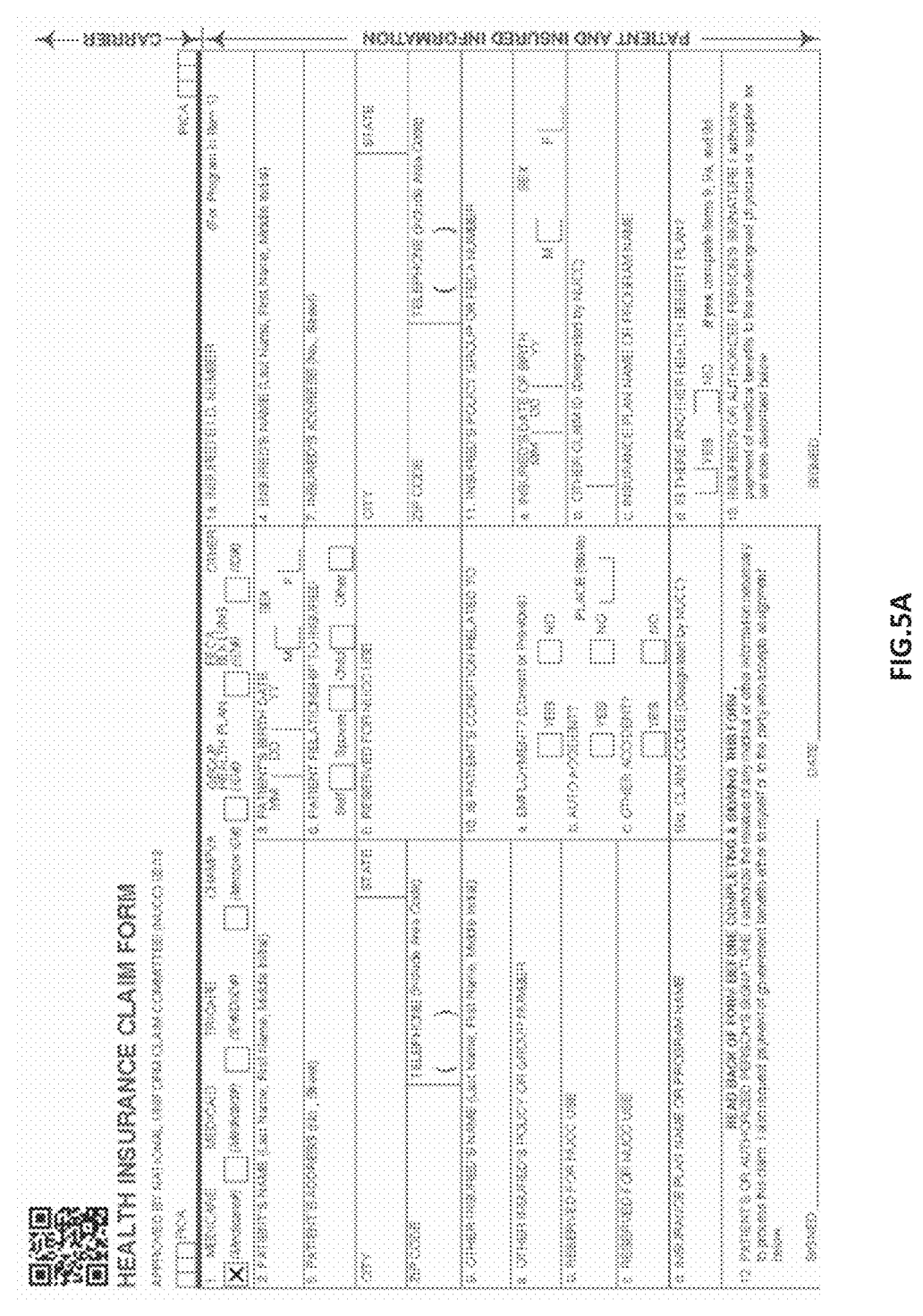
Figure 5B:
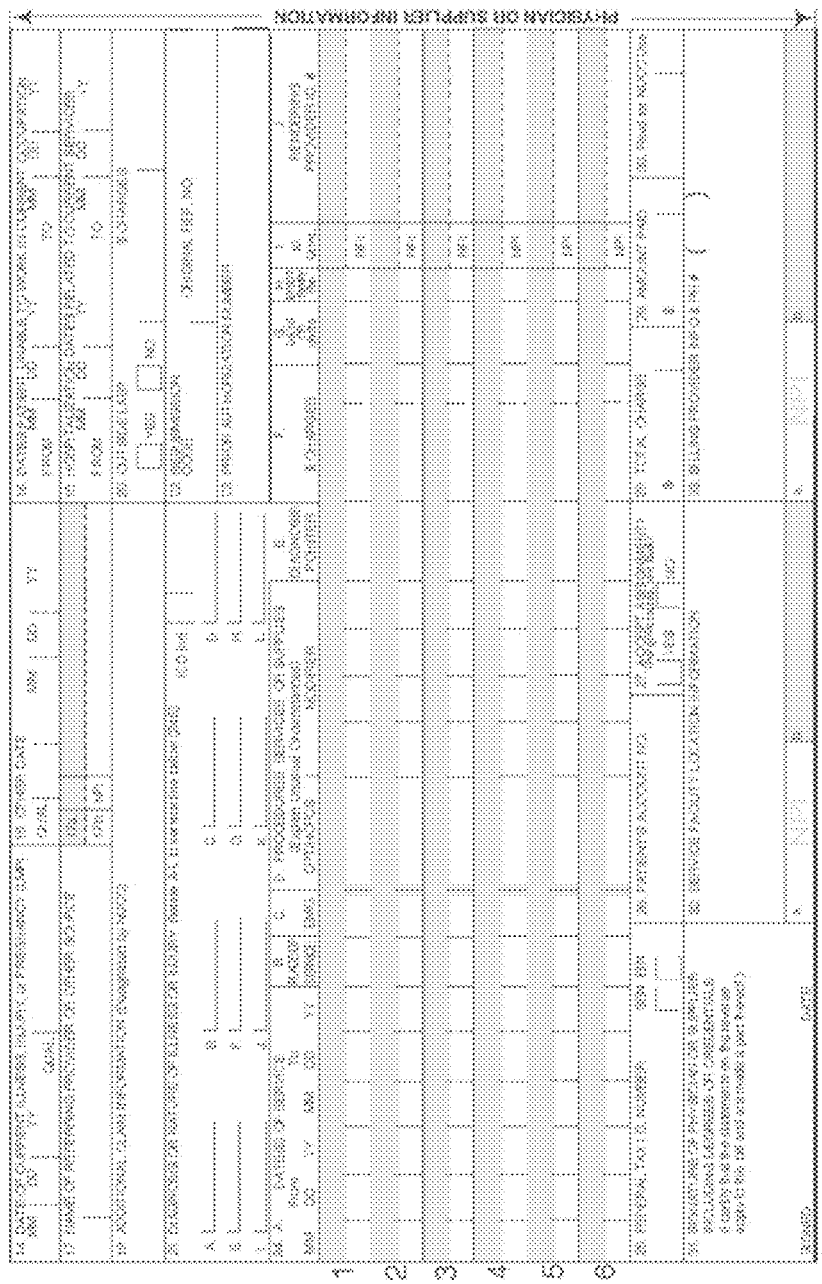

Further, an exemplary claim form 500 has been explained with reference to FIGS. 5A and 5B. The claim form 500 contains information about one or more encounters. In this example, the medical claim form 500 includes 33 fields and some of the fields have sub-fields, such as Field 24 shown in FIG. 4B. The exemplary medical claim form 500 is a type of invoice, where each line in Field 24 is a line item for some service rendered. There may be one or two insurances, where the first is referred to as a primary insurance and the other is referred to as a secondary insurance.

The medical claim form 500 further includes information that goes into a typical medical claim for physical billing. In an example, fields 2, 3, 5 and 26 are used to fill in patient details. Field 24J is used to fill the name of the medical provider. Fields 24B and 32 are used to fill a location of the encounter. Field 24A is used to fill the time of encounter. Fields 1, 4, 6, 7, 9, and 11 are used to fill the name of the payer 114.

Field 24D is used to fill the procedures. In an example, every encounter should contain one or more procedure codes, to denote what the provider did in this encounter. In the context of the present disclosure, a subset of 20 or so codes out of the 10,000 code set from American Medical Association (AMA) may be used. The set is called Common Procedure Terminology (CPT). This subset is a part of the Evaluation and Management (E&M) section of the CPT code set. These are the codes that are most relevant to hospitalists. The CPT code set can be derived from the information obtained from the UI 109 and the hospital software 105. For instance, if the patient has status=Inpatient and if the user has provided an input 'f2 (follow-up level-2' through the UI 109, then it can be inferred from the database 103 that the CPT code is 99232.

Unlike procedure codes, which are required to be determined using the UI 109, the disease codes can be reused from the hospital software 105. The system is configured to fill these codes into Field 21 in the CMS 1500 form. And they are referenced in Field 24E. Mapping disease names to disease codes is commonly referred to as 'medical coding', for diseases, and either the provider himself or a medical coder obtains this mapping.

Field 33 is used to fill the name of person for whom the payment has to be made to. Field 24F is used to fill the amount that has to be paid. This field may be auto-filled by the billing server 102 based on the procedure code filled in the field 24D. The medical claim form 500 includes other information, such as dates of hospitalization, and whether this was an auto incident.

The medical claim form 500 further includes a field for filling details about one or more dates of service, starting with when the patient entered the hospital to when he left. Each visit has a visit ID that is assigned by the hospital, while admitting the patient. The medical claim form 500 further includes a field for filling a Length of stay (LOS), i.e. the count of the number of days in a visit. The medical claim form 500 further includes a field for filling a Medical Record Number (MRN), which identifies a patient, within a hospital or hospital system. So if a patient was admitted 3 times to a hospital, and discharged 2 days later, in the last month, this number will be the same, but there will be 3 visit IDs, one per visit. When that happens, the same patient gets a new number, and this update has to be tracked.

In an embodiment of the present disclosure, the billing server 102 is configured to prepare the claim for all types of doctors (cardiologists, nephrologists, physical therapists etc), other locations (patient's home, skilled nursing facility), other types of billing (lab billing, radiology, when referrals are involved).

The billing server 102 may assemble the information received from the UI 109 and the data sources 112 together into a medical claim and send it to the clearinghouse 106. The clearinghouse 106 may send it over to the payer 114 for the final payment.

Also, in another embodiment of the present disclosure, the original source of the information may be connected directly to the payer 114, so that the information that the billers need to send over. In an embodiment of the present disclosure, once the claim form has been assembled and prepared by the billing server 102, it can be directly shared with the payer 114, instead of sending to the clearing house 106.

Figure 6A:

FIG. 6A illustrates another exemplary screenshot 600 of the UI 109 that shows that a patient called 'Beto, Bob' has been assigned to doctor 'Devi, Uma' on Jul. 14, 2019. The 'charge' for this doctor is in its default state of 'Follow up', 'Select'. This illustrates that the medical provider has not seen this patient yet or has seen but not uploaded his charge yet. For the billing, the medical provider performs the encounter, determines the type of service such as admit, follow-up and discharge. Further, he determines the level of service (1/2/3) depending on what he did in this encounter and uses the screenshot 200 to click the type and level.

Figures 6B, 6C:
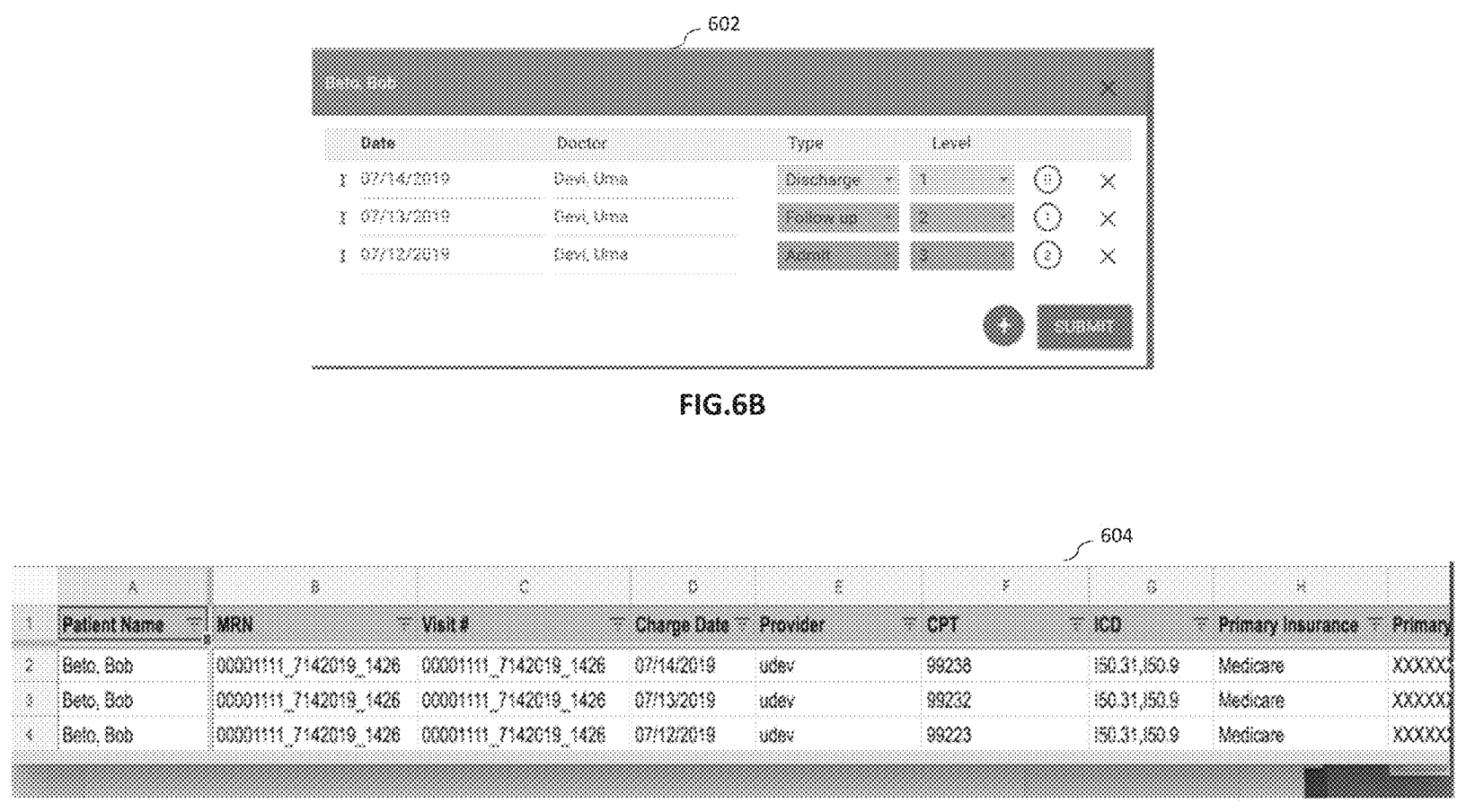

FIG. 6B illustrates another exemplary screenshot 602 of the UI 109 that shows all rows for some patient from when he came into the hospital to when he got discharged. The screenshot 602 shows the 'Ty' and 'Level' fields populated when the medical provider inputs the information using the screenshot 300.

In an embodiment of the present disclosure, the information showed in the screenshot 602 regarding a patient may be shared among multiple parties, for real-time transparency and easy back-and-forth communication when needed. In an example, the information may be downloaded in a spreadsheet 604 (as illustrated with reference to FIG. 6C), and shared with other entities of the environment 100.

In an example, every medical claim in the CMS 1500 form 500 may be modeled as one or more rows in the spreadsheet 604, such that each row has 33 fields. As seen in the spreadsheet 604, the patient has a length-of stay (LOS) of 3 days. Each row corresponds to one day that the patient has stayed in the hospital, and the information about the patient, insurance is repeated for each row. This makes it possible for each row to be processed independently by the payer 114, even if the same information, like 'Beto, Bob' for patient name is repeated in multiple rows. The spreadsheet 604 may be provided with a 'share' button so that it can be shared directly with other entities such as the payer 114, and the clearing house 106, by clicking on the 'share' button. Also, a provision for providing comments can be added in the spreadsheet 604 to enable the payer 114 or the clearing house 106 to add their comments. The spreadsheet can help human communication, between the people in the billing company and payer 114. It can also help automation, via one or more APIs.

In another embodiment of the present disclosure, whenever a row is added in the spreadsheet 604, a transaction may be added in a blockchain that is shared by the billing server 102, the clearinghouse 106, and the payer 114. In this transaction, only the row is added, and does not contain any Protected Health Information (PHI), and the URL of the spreadsheet 604 may be communicated off-chain. The PHI does include the "micro-location" such as room number, bed number, and current time. The blockchain can be added into the flow so that every update to the spreadsheet 604 may be backed up in the blockchain. Whenever a request is sent from the UI 109 to the billing server 102, the details of the request are written as a transaction in the blockchain. In an example, if the request includes {latitude: X, longitude: Y, time: T, doctorId: D, {micro-location: M and/or patientNamePrefix: P}, chargeType: admit (for example), level: 2}, then this information is written into a blockchain. The blockchain technology improves security of the overall system dues to its immutability and decentralization properties.

FIG. 7 illustrates a list 700 of icons that can be added on an 'icon bar' on top of medical documents such as progress note and medical bills. This bar is similar to a barcode, in that it represents the contents of the document in a specific way. This bar acts as a short visual summary for what a medical document is about or what the doctor did. The idea here is to assemble the icons for procedures, diseases, and any others, like medications, lab tests, and show them in a variety of documents, including medical progress notes, discharge summaries, and the billing statements that are sent out to patients.

As per the icons 700, an icon is designed for Hyperglycemia by breaking down into three parts, Hyper 702, glyco 704 and -emia 706. In this case, etymology and etiology (what caused the disease) is being used to come up with the icons, for Lungs (Pneumo), burning (itis) and caused by infection (a symbol for a bug). The icons for 'Hyper' and 'Hypo' can be used and reused for 2 diseases like Hypernatremia or Hypercalcemia. Further, a concept like 'emia' can be shown with a X mark around the symbol for a blood, to mean that -emia means lack of blood.

In another embodiment of the present disclosure, a hover text may be used for each icon. So, if the mouse is moved around the icon for blood, it may say 'blood'. Also, the text may be translated into other languages. Also, a mic icon can be integrated in the translate page, so that the English and native language versions of the individual icons and the complete disease names may be spoken out to the user.

Figure 8:
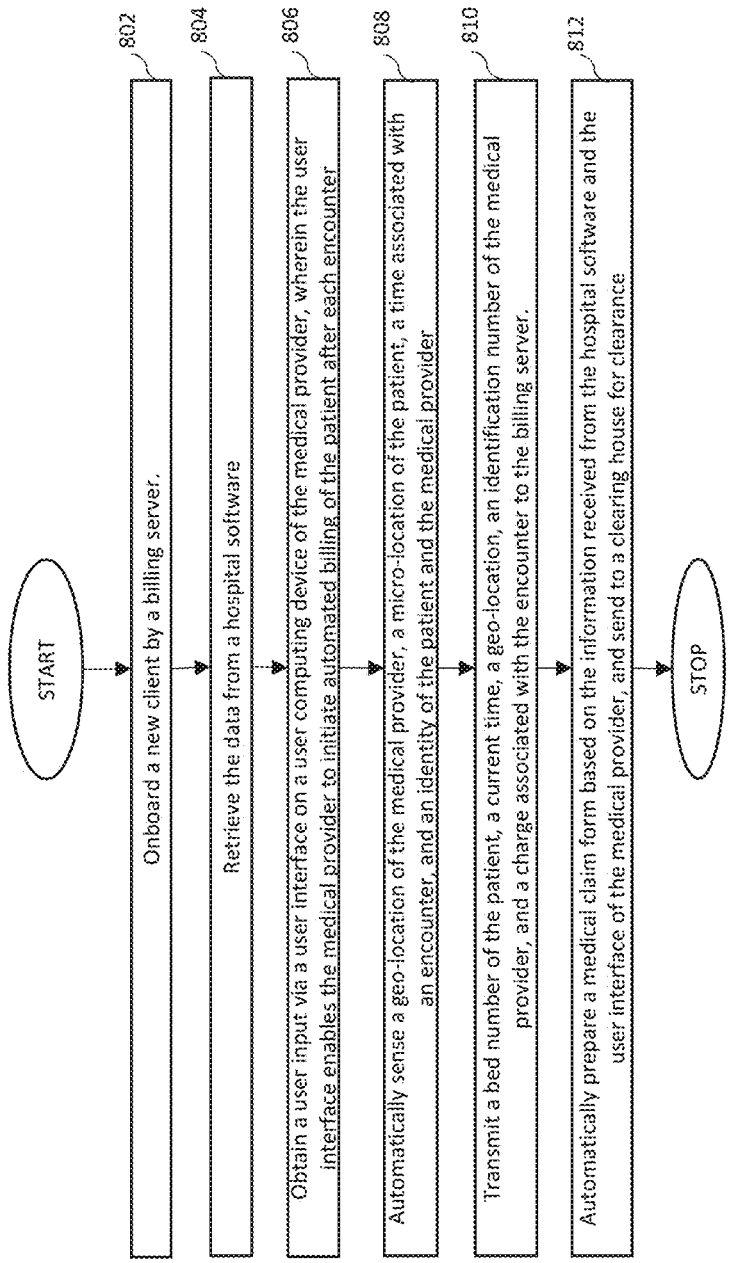
FIG. 8 is a flowchart illustrating a method for automated medical billing, in accordance with an embodiment of the present disclosure.

FIG. 8 is a flowchart illustrating a method for automated medical billing, in accordance with an embodiment of the present disclosure.

At step 802, a new client may be onboarded by a billing server. The new client may include a medical group of hospitalists. In an embodiment of the present disclosure, the new client is required to provide the information about their group, the hospital they work in, the details of doctors, and nurse practitioners, so that they can be used in various fields of the medical claim form. For example, the name and NPI of each hospital, the name, phone, email and NPI of each provider (doctor/midlevel), the name of the billing provider and EIN (the one to whom payment should be sent to) are obtained.

In an embodiment of the present disclosure, the medical information may be updated periodically, when a program coordinator from the medical group sends new information to a billing coordinator (some human being in the billing company) and this may be entered into the billing server. Alternatively, the medical information may be updated directly in an administrator panel of the billing server.

At step 804, the data is retrieved from a hospital software in form of HL7 files. In an example, the hospital software may provide the information twice a day, at 8:00 AM and 8:00 PM each day. The data may include a master list of patients, and for each patient, information such as the insurance provider.

At step 806, a user input is obtained via a user interface on a medical provider computing device, wherein the user interface enables the medical provider to initiate automated billing of the patient after each encounter. In an embodiment of the present disclosure, the charge type and level information regarding a patient may be obtained from the user interface of the medical provider. The medical provider may provide this information as soon as they visit the patient.

At step 808, a geo-location of the medical provider, a micro-location of the patient in hospital, a time associated with an encounter, and an identity of the patient and the medical provider are automatically sensed, wherein the micro-location includes a bed number of the patient in the hospital.

At step 810, a bed number of the patient, a current time, a geo-location, an identification number of the medical provider, and a charge associated with the encounter are transmitted to the billing server. In an embodiment of the present disclosure, the charge may be manually input by the medical provider. In another embodiment of the present disclosure, the charge may be automatically derived by the billing server based on the disease type details.

At step 812, a medical claim form is automatically prepared based on the information received from the hospital software and the user interface of the medical provider, and sent to a clearing house for clearance. In case of any error in the claim form, the patient/user may be notified through a SMS or email. In an embodiment of the present disclosure, the billing server is configured to analyze each and every field of the form, determine which fields can be populated with data obtained from other sources, like NPPES. The billing server is further configured to determine which fields have to be filled only once, when a new group signs and which fields change per encounter, like Field 24. The billing server is further configured to populate the claim form based on the patient details, encounter details, and medical provider details obtained from the hospital software and the assistant module.

Various embodiments of the present disclosure facilitate reducing the number of fields a user has to fill in, by pulling in information from other related sources and reconciling. They further facilitate reducing the cognitive load in data entry forms, with the help of icons for disease codes and procedure codes. They furthermore facilitate using the simple share button to connect providers, billers, patients and payers, who are everyday Internet users.

What is claimed is:

1. A method for automated medical billing, the method comprising:
    retrieving details of one or more encounters between a patient and a medical provider from a hospital software;
    obtaining a user input via a user interface on a medical provider computing device, wherein the user interface enables the medical provider to initiate automated billing of the patient after each encounter from the user input including, a maximum of, initials of the patient, a type of service to the patient by the medical provider and a level of service to the patient by the medical provider;
    automatically sensing a geo-location of the medical provider, a micro-location of the patient in hospital, a time associated with an encounter, and an identity of the patient and the medical provider, wherein the micro-location includes a bed number of the patient in the hospital;
    transmitting a bed number of the patient, a current time, a geo-location, an identification number of the medical provider, and a charge associated with the encounter to the billing server;
    automatically filling a claim form on the user interface by the billing server, based on the received information; and
    directly transmitting the filled claim form from the user interface to a payment entity including at least one of: a payer and a clearing house, wherein transmitting the filled claim form includes representing the information regarding the filled claim form in a spreadsheet, encrypting the spreadsheet using blockchain and sharing the filled claim form in the form of the encrypted spreadsheet directly with the payment entity.

2. The method of claim 1, wherein the micro-location of the patient inside the hospital is automatically sensed using a beacon device fixedly configured at a bedside or placed in a pocket of a gown worn by the patient or a bracelet worn by the patient.

3. The method of claim 1, wherein the micro-location of the patient inside the hospital is automatically sensed using a drone assigned to the patient room.

4. The method of claim 1, wherein each update to the spreadsheet is backed-up using blockchain technology.

5. The method of claim 1 further comprising automatically recognizing a voice of the medical provider and initiating one or more actions in the user interface accordingly.

6. The method of claim 1 further comprising adding, by the medical provider, one or more icons on the user interface corresponding to the patient, wherein the one or more icons are representative of procedures, diseases, medications, lab tests in medical progress notes, discharge summaries, and billing statements.

7. A system for automated medical billing, the system comprising:
    a billing server configured to:
        retrieve details of one or more encounters between a patient and a medical provider from a hospital software;
        obtain a user input via a user interface on a user computing device of the medical provider, wherein the user interface enables the medical provider to initiate automated billing of the patient after each encounter, wherein the user input includes, a maximum of, initials of the patient, a type of service to the patient by the medical provider and a level of service to the patient by the medical provider;
    an assistant module configured to:
        automatically sense a geo-location of the medical provider, a micro-location of the patient in hospital, a time associated with an encounter, and an identity of the patient and the medical provider, wherein the micro-location includes a bed number of the patient in the hospital; and
        transmit a bed number of the patient, a current time, a geo-location, an identification number of the medical provider, and a charge associated with the encounter to the billing server,
    wherein the billing server is configured to automatically fill a claim form on the user interface based on the received information, and directly send the filled claim form from the user interface to a payment entity including one of:
    a payer and a clearing house, wherein sending the filled claim form includes representing the information regarding the filled claim form in a spreadsheet, encrypting the spreadsheet using blockchain and sharing the filled claim form in the form of the encrypted spreadsheet directly with the payment entity.

8. The system of claim 7, wherein the assistant module includes a beacon device for automatically sensing the micro-location of the patient inside the hospital, and wherein the beacon device is fixedly configured at a bedside or placed in a pocket of gown worn by the patient.

9. The system of claim 7, wherein the assistant module includes a drone assigned to the patient for automatically sensing the micro-location of the patient inside the hospital.

10. The system of claim 7, wherein each update to the spreadsheet is backed-up using blockchain technology.

11. The system of claim 7 further comprising an automatic voice recognition module configured to automatically recognizing a voice of the medical provider and initiating one or more actions in the user interface accordingly.

12. The system of claim 7, wherein the billing server is configured to add one or more icons, via inputs by the medical provider, on the user interface, and wherein the one or more icons are representative of procedures, diseases, medications, lab tests in medical progress notes, discharge summaries, and billing statements.

13. A computer programmable product for automated medical billing, the computer programmable product comprising a set of instructions, the set of instructions when executed by a processor causes the processor to:

retrieve details of one or more encounters between a patient and a medical provider from a hospital software;

provide a user interface on a user computing device of the medical provider, wherein the user interface enables the medical provider to initiate automated billing of the patient after each encounter, wherein the user input includes, a maximum of, initials of the patient, a type of service to the patient by the medical provider and a level of service to the patient by the medical provider;

automatically sense a geo-location of the medical provider, a micro-location of the patient in hospital, a time associated with an encounter, and an identity of the patient and the medical provider, wherein the micro-location includes a bed number of the patient in the hospital;

transmit a bed number of the patient, a current time, a geo-location, an identification number of the medical provider, and a charge associated with the encounter to the billing server;

automatically fill a claim form on the user interface by the billing server, based on the received information; and directly send the filled claim form from the user interface to a payment entity including at least one of: a payer and a clearing house, wherein sending the filled claim form includes representing the information regarding the filled claim form in a spreadsheet, encrypting the spreadsheet using blockchain, and sharing the filled claim form in the form of the encrypted spreadsheet directly with the payment entity.

* * * * *